United States Patent
Jamil

(10) Patent No.: US 11,541,024 B2
(45) Date of Patent: Jan. 3, 2023

(54) STABLE IBUPROFEN INJECTABLE COMPOSITION

(71) Applicant: Ambah IP Limited

(72) Inventor: Irfan Jamil, Jeddah (SA)

(73) Assignee: AMBAH IP LIMITED, Qormi (MT)

( * ) Notice: Subject to any disclaimer, the term of this patent is extended or adjusted under 35 U.S.C. 154(b) by 0 days.

(21) Appl. No.: 16/322,569

(22) PCT Filed: Jul. 27, 2017

(86) PCT No.: PCT/IB2017/054556
§ 371 (c)(1),
(2) Date: Feb. 1, 2019

(87) PCT Pub. No.: WO2018/025128
PCT Pub. Date: Feb. 8, 2018

(65) Prior Publication Data
US 2019/0183823 A1      Jun. 20, 2019

(30) Foreign Application Priority Data
Aug. 2, 2016  (PK) ..................................... 468/2016

(51) Int. Cl.
| | |
|---|---|
| A61K 31/192 | (2006.01) |
| A61K 9/00 | (2006.01) |
| A61K 47/18 | (2017.01) |
| A61K 47/26 | (2006.01) |
| A61K 9/08 | (2006.01) |
| A61P 25/00 | (2006.01) |

(52) U.S. Cl.
CPC .......... *A61K 31/192* (2013.01); *A61K 9/0019* (2013.01); *A61K 9/08* (2013.01); *A61K 47/183* (2013.01); *A61K 47/26* (2013.01); *A61P 25/00* (2018.01)

(58) Field of Classification Search
CPC ....... A61K 31/192; A61K 9/0019; A61K 9/08
See application file for complete search history.

(56) References Cited

U.S. PATENT DOCUMENTS 5,116,955 A * 5/1992 Langfeld ................. C09B 33/04
                                                                534/582
6,887,462 B2   5/2005 Shirley et al.
2008/0075689 A1 * 3/2008 Pierobon ............... A61K 8/8182
                                                                424/78.27
2013/0217772 A1 * 8/2013 Selmi ................... A61K 9/0019
                                                                514/565
2015/0208705 A1 * 7/2015 Galaffu .................... A23L 5/43
                                                                426/540

FOREIGN PATENT DOCUMENTS

| | | | |
|---|---|---|---|
| CN | 101069681 | * | 5/2006 |
| CN | 101069681 | * | 11/2007 |
| CN | 101069681 A | | 11/2007 |
| CN | 103284985 | * | 5/2013 |
| CN | 103284985 A | | 9/2013 |
| CN | 103301118 | * | 9/2013 |
| CN | 103301118 A | | 9/2013 |
| CN | 101069681 | * | 11/2017 |
| ES | 2422563 | * | 9/2013 |
| ES | 2422563 A1 | | 9/2013 |
| ES | 2422563 | * | 10/2014 |
| WO | WO 2003/039532 | * | 5/2003 |
| WO | 2006081587 A2 | | 8/2006 |
| WO | 2007103782 A2 | | 9/2007 |
| WO | WO 2016/009067 | * | 1/2016 |

OTHER PUBLICATIONS

Beijing Fukangren Biopharmaceutical Technology (Sep. 2013) (Year: 2013).*
Hi Media Cell Culture product information (2011) (Year: 2011).*
Decision of Rejection (English) in JP2019-506368, dated Dec. 21, 2021.

* cited by examiner

*Primary Examiner* — Marcos L Sznaidman

(74) *Attorney, Agent, or Firm* — Elmore Patent Law Group, P.C.; Joseph C. Zucchero; Carolyn S. Elmore

(57) ABSTRACT

The present invention relates to a composition for injectable formulation, the composition comprising: —An aqueous solution of ibuprofen and arginine with a molar ratio of ibuprofen:arginine comprised between 1:1.1 and 1:2.1; —An aqueous solution of a diuretic compound comprising between 3.9% and 4.35% w/v of the diuretic compound. The present invention also concerns a pharmaceutical composition comprising said composition and the use of said composition and said pharmaceutical composition.

21 Claims, No Drawings

STABLE IBUPROFEN INJECTABLE COMPOSITION

RELATED APPLICATIONS

This application is a US National stage entry of International Application No. PCT/IB2017/054556, which designated the United States and was filed on Jul. 27, 2017, published in English, which claims the benefit of priority Application No. PK468/2016, filed on Aug. 2, 2016. The entire teachings of the above applications are incorporated herein by reference.

TECHNICAL FIELD

The present invention relates to a composition for injectable formulation and to a pharmaceutical composition comprising thereof. The invention also concern the use of the composition and of the pharmaceutical composition.

INTRODUCTION

There are different problems associated to post operative pain and fever that are normally due to respiratory, cardio circulatory, digestive, metabolic, immunological, urological, musculoskeletal and psychological complications.

Ibuprofen is a well known non-steroidal anti-inflammatory drug with antipyretic and analgesic activities. Poor solubility of Ibuprofen in water always remains an obstacle to develop a stable injectable formulation.

Different combinations of Ibuprofen with amino acids were developed to solubilize Ibuprofen in water.

The existing claimed formulations available for Ibuprofen injectable contain combination of Ibuprofen with Arginine with different molar ratios for concentrate and ready to use products.

Cardolor a leading market product is 100 mg/mL Ibuprofen concentrate, a combination of Ibuprofen and Arginine with molar ratio 1:0.92, require 0.9% Sodium Chloride, 5% dextrose or Ringer's lactate solution to make 4 mg/mL of Ibuprofen isotonic intravenous solution. Claimed pH is about 7.6 but stability of diluted solution in 0.9% sodium chloride and 5% dextrose is about 24 hours maximum and pH of diluted solution is about 6 at room temperature.

Other ready to use formulations also contains Ibuprofen and Arginine with different molar ratios use 0.9% sodium chloride as osmotic agent. Trometamol or salts of sodium and potassium are used as buffering agent.

Extra sodium in bloodstream may increase blood pressure and is not suitable for patients at low sodium intake. Increased amount of sodium in bloodstream may increase the risk of heart and stroke.

Buffers are used to stabilize the pharmaceutical liquid formulations. All ready to use Ibuprofen formulation are practically stable at pH 7.8 to 9.0 as result increase blood pH. Increased blood pH may increase blood coagulation time. Using such intravenous solutions extreme care is required to avoid perivascular infiltration. Local tissue damage and subsequent sloughing may occur if extra vasation occurs.

Therefore known compositions with solubilized ibuprofen present several drawbacks. That is why, one aim of present invention is to provide a composition with solubilized ibuprofen and exempt from, or minimizing, the drawbacks of the known compositions.

Another aim of present invention is to provide an aqueous, sodium free, dextrose free and buffer free stable Ibuprofen Injectable formulation.

SUMMARY OF INVENTION

The composition according to the independent claims provides a composition or a pharmaceutical composition exempt from, or minimizing the drawbacks of the known composition of above mentioned problems. Dependent claims describes optional features.

The present invention provides a composition with a solubilized ibuprofen thanks to an aqueous solution of ibuprofen and arginine with a molar ratio of ibuprofen: arginine comprised between 1:1.1 and 1:2.1, in combination with a aqueous solution of a diuretic compound comprising between 3.9% and 4.35% w/v of the diuretic compound.

Advantageously, the composition according to the present invention comprises a perfect combination ratio of Ibuprofen and Arginine in diuretic solution that eliminates the requirement of any buffer and pH adjustment or other additive and the known drawbacks related thereof.

The composition according to the invention also provides a stable ibuprofen composition for injectable formulation.

The present invention is an excellent analgesic treatment, for use in hospitals, for post operative pain and fever. The present invention, due to its rout of administration, can provide the patient an early recovery, as well as reduce the time of hospitalization and cost associated to the patient care.

The current invention is sodium free, dextrose free and buffer free stable Ibuprofen intravenous injection or infusion. Sodium free, dextrose free and buffer free stable Ibuprofen intravenous injection or infusion increases the scope of application of current invention over existing marketed Ibuprofen injectable products and can help to optimize the safety and clinical efficacy of the patient as well as reduce the risk of disorders that may associated with cardiovascular system, hypertension, diabetic, perivascular infiltration and local tissue damage.

For usage of present invention in high fever and normal body temperature pH of solution is very near to blood pH. At 37° C. pH is 7.47, at 38° C. pH is 7.41, at 39° C. pH is 7.38. Present invention is stable at real time and accelerated stability conditions as per ICH guidelines.

In one embodiment, the composition comprises mannitol as osmotic agent making current invention Sodium free and dextrose free.

In one embodiment, the pH for stability Ibuprofen infusion solution is 8.20 at 20° C. (measured as per requirement of European Pharmacopeia) 8.04 at 25° C. and 7.87 at 30° C.

In one embodiment, the composition is an aqueous, sodium free, dextrose free and buffer free stable Ibuprofen Injectable formulation with molar concentration of ibuprofen to arginine (1:1.9908-1:1.22388) in 4.05%-4.25% w/v solution of mannitol in WFI with temperature dependent pH.

In one embodiment, arginine is replaced by another nitrous oxide or nitric oxide precursor.

In one embodiment, ibuprofen is replaced by another analgesic compound, for instance ibuprofen derivatives, or analgesic compound with similar solubility's properties.

The invention claimed is:

1. Aqueous ibuprofen injectable formulation consisting of arginine and solubilized ibuprofen in a diuretic solution of mannitol in water for injection (WFI);

wherein the molar ratio of ibuprofen:arginine is between 1:1.22388 and 1:1.9908 or between 1:1.22 and 1:1.99, the diuretic solution of mannitol comprises between 4.05% to 4.25% w/v of mannitol and the concentration of ibuprofen is between 1 mg/mL and 8 mg/m/L or between 25 mg/mL and 200 mg/mL.

2. The aqueous ibuprofen injectable formulation according to claim 1, wherein the pH of the injectable formulation is 7.47 at 37° C., 7.41 at 38° C. and 7.38 at 39° C., measured as per requirement of European Pharmacopeia.

3. The aqueous ibuprofen injectable formulation according to claim 1, wherein the pH of the injectable formulation is 8.20 at 20° C., measured as per requirement of European Pharmacopeia.

4. The aqueous ibuprofen injectable formulation according to claim 1, wherein the molar ratio of ibuprofen:arginine is between 1:1.22388 and 1:1.22.

5. The aqueous ibuprofen injectable formulation according to claim 4, wherein the molar ratio of ibuprofen:arginine is 1:1.22388 or 1:1.22.

6. Pharmaceutical composition consisting of the injectable ibuprofen formulation according to claim 1, wherein the concentration of ibuprofen is between 1 mg/mL-8 mg/mL.

7. Pharmaceutical composition consisting of the injectable ibuprofen formulation according to claim 1, wherein the concentration of ibuprofen is between 25 mg/mL-200 mg/mL.

8. The pharmaceutical composition according to claim 6, wherein the pharmaceutical composition is stable for 48 months in glass bottle with a stopper selected from a rubber or aluminum cap.

9. The pharmaceutical composition according to claim 6, wherein the pharmaceutical composition is stable for 48 months in a plastic bottle.

10. The pharmaceutical composition according to claim 6, wherein the pharmaceutical composition is stable for 48 months in polymer bags.

11. The pharmaceutical composition according to claim 6, wherein said pharmaceutical composition is prepared aseptically.

12. The pharmaceutical composition according to claim 6, wherein said pharmaceutical composition is autoclavable at a temperature around 121° C.

13. The aqueous ibuprofen injectable formulation according to claim 1 or pharmaceutical composition according to claim 6, for use in an analgesic treatment of a patient.

14. The pharmaceutical composition according to claim 7, wherein the pharmaceutical composition is stable for 48 months in a glass bottle with stopper selected from a rubber or aluminum cap.

15. The pharmaceutical composition according to claim 7, wherein the pharmaceutical composition is stable for 48 months in a plastic bottle.

16. The pharmaceutical composition according to claim 7, wherein the pharmaceutical composition is stable for 48 months in polymer bags.

17. The pharmaceutical composition according to claim 7, wherein said pharmaceutical composition is prepared aseptically.

18. The pharmaceutical composition according to claim 7, wherein said pharmaceutical composition is autoclavable at a temperature around 121° C.

19. The aqueous ibuprofen injectable formulation according to claim 1, wherein the pH of the injectable formulation is between 7.4 and 8.2 within the temperature range of 20° C. to 39° C., measured as per requirement of European Pharmacopeia.

20. The pharmaceutical composition according to claim 9, wherein the plastic bottle is made of LDPE, HDPE, PP or COC.

21. The pharmaceutical composition according to claim 15, wherein the plastic bottle is made of LDPE, HDPE, PP or COC.

* * * * *